(12) United States Patent
Cavanaugh (10) Patent No.: US 9,289,524 B1
(45) Date of Patent: Mar. 22, 2016

(54) APPARATUS TO SELECTIVELY USE UV TO CONTROL ORGANISMS ASSOCIATED WITH PLANTS AND UNWANTED PLANT SPECIES

(71) Applicant: Floratine Products Group, Inc., Collierville, TN (US)

(72) Inventor: Kevin Cavanaugh, Ponte Vedra Beach, FL (US)

(73) Assignee: Floratine Products Group, Inc., Collierville, TN (US)

( * ) Notice: Subject to any disclaimer, the term of this patent is extended or adjusted under 35 U.S.C. 154(b) by 0 days.

(21) Appl. No.: 14/519,379

(22) Filed: Oct. 21, 2014

Related U.S. Application Data

(62) Division of application No. 13/894,499, filed on May 15, 2013, now Pat. No. 8,911,664.

(60) Provisional application No. 61/736,105, filed on Dec. 12, 2012, provisional application No. 61/684,723, filed on Aug. 18, 2012, provisional application No. 61/647,070, filed on May 15, 2012.

(51) Int. Cl.
*A61L 2/00* (2006.01)
*A61N 5/00* (2006.01)
*A01B 77/00* (2006.01)
*G01N 23/00* (2006.01)
*A61L 2/10* (2006.01)

(52) U.S. Cl.
CPC ........................................ *A61L 2/10* (2013.01)

(58) Field of Classification Search
CPC ................ A61L 2/00; A61L 9/18; A61L 9/20
USPC .................. 422/1, 22, 24; 250/455.11, 492.1; 47/1.42; 219/700; 15/319, 339
See application file for complete search history.

(56) References Cited

U.S. PATENT DOCUMENTS

2009/0272029 A1 11/2009 Aiking et al.
2011/0274582 A1* 11/2011 Davis ....................... A61L 2/10
422/24

* cited by examiner

*Primary Examiner* — Monzer R Chorbaji
(74) *Attorney, Agent, or Firm* — Harris, Shelton, Hanover & Walsh; Susan B. Fentress (57) ABSTRACT

The present invention relates to a device for reducing the total number of pathogens of one or more pathogen living in turf. This invention provides a number of devices to safely deliver the UV light to plants. In one embodiment, the device is made of a plurality of UV emitting devices imbedded in a face of a stationary bed knife blade. The plurality of UV emitting devices forming an arc of substantially continuous UV coverage. This modified bed-knife can be incorporated into a lawn mower to provide UV radiation, while at the same time cutting the turf.

5 Claims, 12 Drawing Sheets
(6 of 12 Drawing Sheet(s) Filed in Color)

APPARATUS TO SELECTIVELY USE UV TO CONTROL ORGANISMS ASSOCIATED WITH PLANTS AND UNWANTED PLANT SPECIES

CROSS REFERENCE TO RELATED APPLICATIONS

This application is a divisional application of U.S. non-provisional application Ser. No. 13/894,499 filed 15 May 2013, and claims the benefit of U.S. provisional 61/736,105 filed 12 Dec. 2012, U.S. provisional application 61/684,723 filed 18 Aug. 2012, U.S. provisional application 61/647,070 filed 15 May 2012, under 35 USC §119(e) (all prior benefit claimed applications referenced hereinabove are hereby incorporated in their entirety by the reference).

BACKGROUND OF THE INVENTION (1) Field of the Invention

This invention is directed to a method for delivering UV light to plants, crops and ornamentals for the purposes of killing bacteria, molds, algae, and fungi or unwanted plant species. Presently, turf based pathogens are destroyed or controlled with the use of harsh chemical treatments. This chemical treatment may be harmful to the environment. A need exists to treat turf based pathogen without potential harm to the environment.

(2) Description of the Related Art

UV light sterilization is a process by which ultraviolet radiation is used to kill microorganisms, molds, algae, and fungi in various environmental applications. UV sterilization is used for air purification systems, water purification, aquarium and pond maintenance, laboratory hygiene and food and beverage protection. UV treatment generally takes place only inside a specialized UV exposure chamber. It is useful for targeted elimination of microorganisms in air and water. UV sterilization leaves no residual chemical or radiation in the air or water and is harmless to untargeted animals and plants. UV sterilization works well in applications where you want to clean up large quantities of microorganisms in air and water in aquariums, ponds, laboratories and clean rooms without leaving liquid or aerosol chemical residue behind.

UV light kills organisms by damaging the DNA. UV radiation disrupts the chemical bonds that hold the atoms of DNA together in the microorganism. If the damage is severe enough, the microorganisms cannot repair the damage and will die. Ultraviolet light penetrates the cells, but does not alter the water, air or food being treated. Nothing is added to the medium other than energy. Dead bugs, organic or inorganic particles are not removed from the sterilized medium. UV radiation is indicated in situations where chemical residue after sterilization is not acceptable. Chemical residue in most crop protectants is significant in terms of chemical half-life deterioration and can and does impact environmental surroundings including introduction to groundwater and waterways. Chemical residue such as this has the ability for altering life cycling, DNA and evolution of plants, animals and humans.

Ultraviolet light is very effective for killing some germs. Airborne bacteria and bacteria on the outer surface of a plant part are easily killed by UV light. Ultraviolet light is part of the electromagnetic spectrum with wavelengths from 10 to 400 nanometers. UV is divided into long wavelength, medium wavelength and short wavelength frequencies. Medium wavelength UV radiation is the light that is used to disinfect food, air, water and the surface of objects such as surgical utensils.

Medium wavelength UV light, between 300-100 nanometers, kills microorganisms because it has mutagenic effect on them. This wavelength of light has an energy level per photon emitted of 4.13 to 6.20 electron volts. UV light in this range breaks down the DNA structure of microorganisms exposed to it and prevents them from reproducing, effectively killing the organism. UV radiation is known to be effective against bacteria, molds and parasites such as dust mites and lice. Staph, perfigens and *E. coli* are killed by UV radiation as are tuberculosis and viral infectious agents. Laboratories, hospitals and college research facilities utilize UV light to sterilize equipment, clothing and utensils. Many labs use 254 nanometer UV lamps to disinfect Petri dishes, beakers and other small utensils.

Ultraviolet (UV) light has been long used for disinfection and sterilization. Ultraviolet light may be produced artificially by electric-arc lamps. Recently, the widespread availability of low to medium pressure mercury bulbs has led to the development of devices which use UV-C to decontaminate water supplies. UV-C is a short wave (280-100 nm) of light within the ultraviolet band and has been shown to be the most bactericidal type of ultraviolet light; more specifically UV-C includes germicidal ultraviolet at 253.7 nm wavelength which is used for air, surface and water disinfection.

BRIEF SUMMARY OF THE INVENTION

In one embodiment, this invention provides a method for reducing the total number of pathogens of one or more pathogen living in turf. This is accomplished by contacting an area of turf with an UV emitting device to provide a sufficient level of radiation necessary to reduce the total number of pathogens, of one or more pathogens, living in the turf, without killing plants and simultaneously cutting the turf in the same area. The term simultaneously cutting a plurality of blades of turf, means that the same apparatus that cuts the turf also provides the UV emitting rays to reduce the total number of pathogens, in the same area of turf.

In one embodiment, a device is made of a plurality of UV emitting devices imbedded in a face of a stationary bed knife blade. The plurality of UV emitting devices forms an arc of substantially continuous UV coverage. This device can be used in a lawn mower with reel blades and the stationary bed knife blade.

In another embodiment, this invention provides a hand propelled device for reducing the total number of pathogens of one or more pathogen living in plants selected from the group consisting: of turf, foliage or shrubs made of a frame connected to a handle at one end and an UV emitting device at a second end, wherein the UV emitting device provides a sufficient level of radiation necessary to reduce the total number of pathogens of one or more pathogen living in the plants without killing the plants and a light shroud of sufficient size to protect an operator from UV radiation and a power source to operate the device.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of the present invention. The invention may be better understood by reference to one or more of these drawings in combination with detailed description of specific embodiments presented herein.

For a fuller understanding of the nature and desired objects of the present invention, reference is made to the following detailed description taken in conjunction with the accompanying drawing FIGS.

DETAILED DESCRIPTION OF THE INVENTION

This invention provides a device and method of substantially reducing plant pathogens using ultraviolet radiation for use in the maintenance of golf courses, commercial landscaping and home use. The present invention relates to the use of UV light to be administered to the pathogenic affected plants or crops at a UV wavelength light, between 400-100 nanometers. This invention provides devices to safely deliver the UV light to plants.

The present invention may be understood more readily by reference to the following detailed description of the invention. It is to be understood that this invention is not limited to the specific devices, methods, conditions, or parameters described herein, and that the terminology used herein is for the purpose of describing particular embodiments by way of example only and is not intended to be limiting of the claimed invention.

The present invention may be understood more readily by reference to the following detailed description of the invention. It is to be understood that this invention is not limited to the specific devices, methods, conditions or parameters described herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

Figure 1:
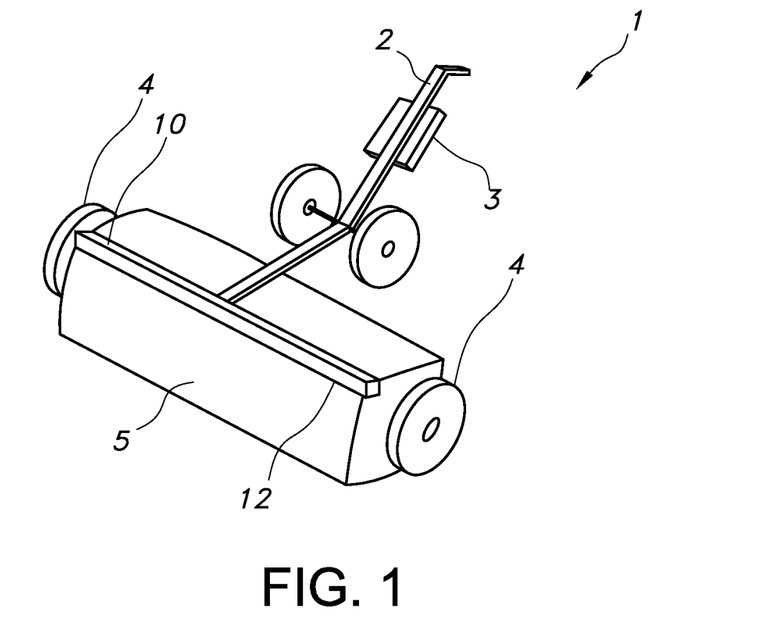
FIG. 1 shows a device to provide UV light to plants.

Now referring to FIG. 1, the apparatus 1 includes a handle 2, a power source 3, such as a lithium battery, and at least one wheel 4 to support a light housing 10 at least one wheel 4 contacting the device and the ground. The light housing 10 is covered by a light shroud 5. The light shroud 5 protects the operator from the UV light. The light shroud 5 can be made of a metal or an UV impermeable plastic. The light housing 10 is mounted about 12 inches above the ground at a preferred angle of about 50 degrees. A light 12 held by the light housing 10 emits UV light at the desired wavelength. In the preferred embodiment, the light is UV-C A 3W T3 germicidal 2.48 inch long E15 lamp (UPC 0487777247495) is preferably used. This apparatus 1 can be used to reduce the total number of one or more pathogens on a living plant. The plants include: turf, foliage or shrubs.

Figure 2:
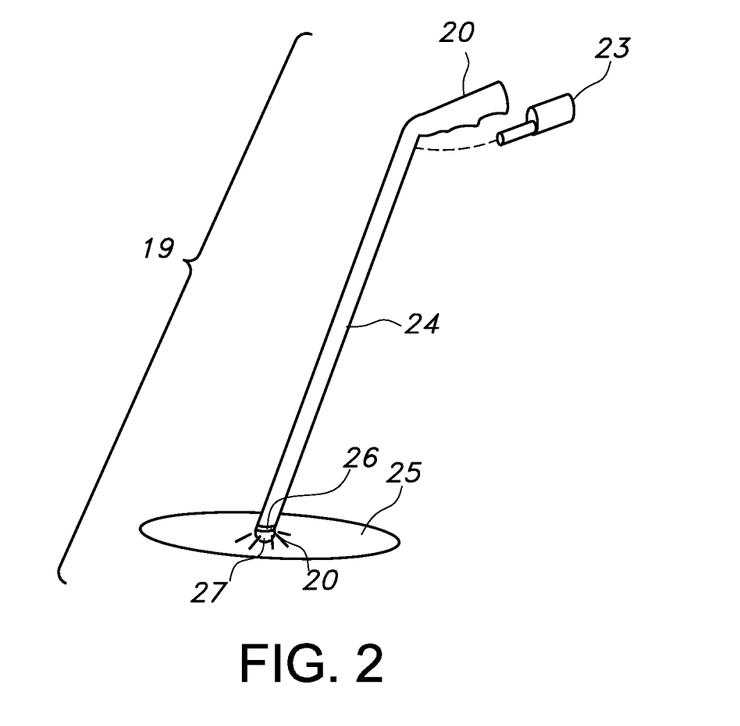
FIG. 2 shows an embodiment of a device to provide UV light to plants.

Now referring to FIG. 2 another embodiment of the device is shown. In this embodiment, a hand held device 19 is provided for reducing the total number of pathogens of one or more pathogens living in plants. The hand held device 19 is made of a frame connector 24 connected to a handle 20 at one end of the frame. A UV emitting device 27 is located at the other end of frame 24. The UV emitting device 27 provides a sufficient level of radiation necessary to reduce the total number of pathogens of one or more pathogens living in the plants without killing the plants. The light housing 26 holds a light emitting device 27 that emits UV light at the desired wavelength. A light shroud 25 is of a sufficient size and is configured to protect an operator from UV radiation emitted by the UV emitting device 27. The hand held device 19 also includes a power source 23 to operate the device 19. In one embodiment, a handle grip 20 is configured to retain a power source 23, such as a lithium battery. The handle grip 20 is connected via frame connector 24 to a domed shroud 25 that hold light housing 26.

Figure 3A:
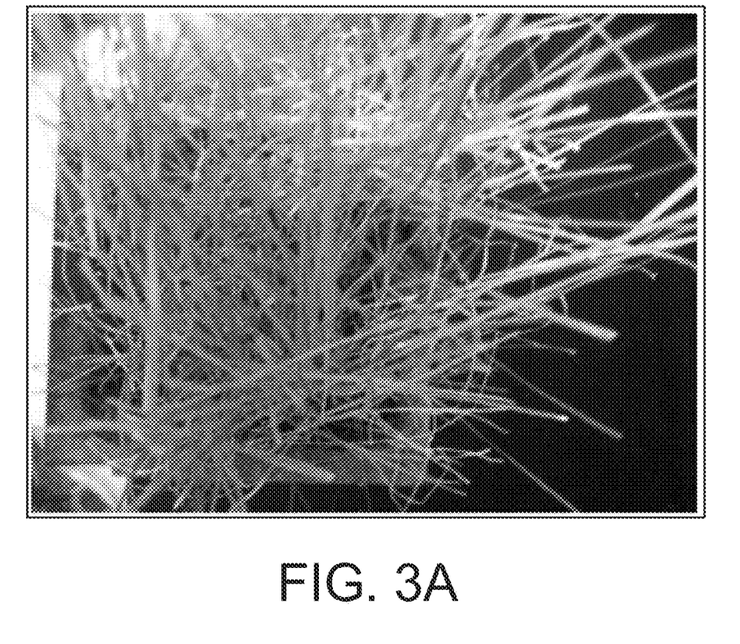
FIG. 3A shows photographs of plants treated with a device to provide UV light to plants.
Figure 3B:
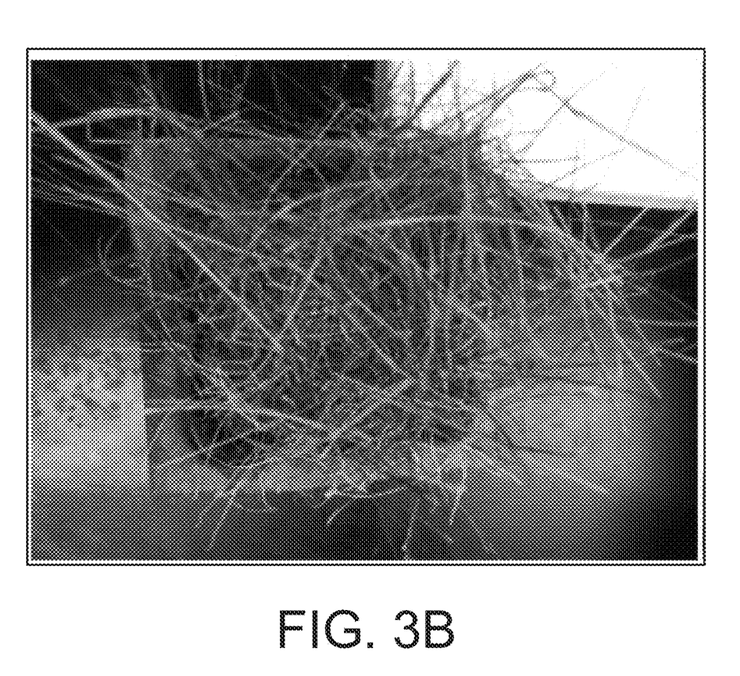
FIG. 3B shows photographs of plants treated with a device to provide UV light to plants.

FIGS. 3A and 3B, shows a test run to establish if turf would be harmed irreparably from intense UVC light. In this experiment, turf (rye) (FIG. 3A prior to exposure) was left under a UVC light fixture for 24 hours at a height of seven (7") inches from bottom of turf container to bottom of light fixture. The turf plot did dry-out considerably (FIG. 3B), but is alive and rebounding. It is not our intention to ever have the need to use the UVC light for that long of duration; but to establish a baseline for the effects of UV-C for a 24 hour period.

Figure 4A:
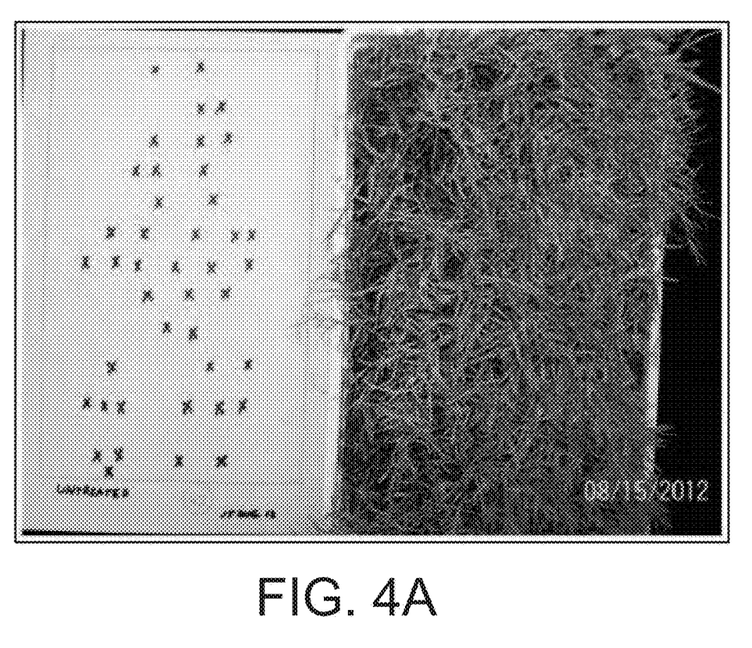
FIG. 4A shows photographs of plants treated with a device to provide UV light to plants.
Figure 4B:
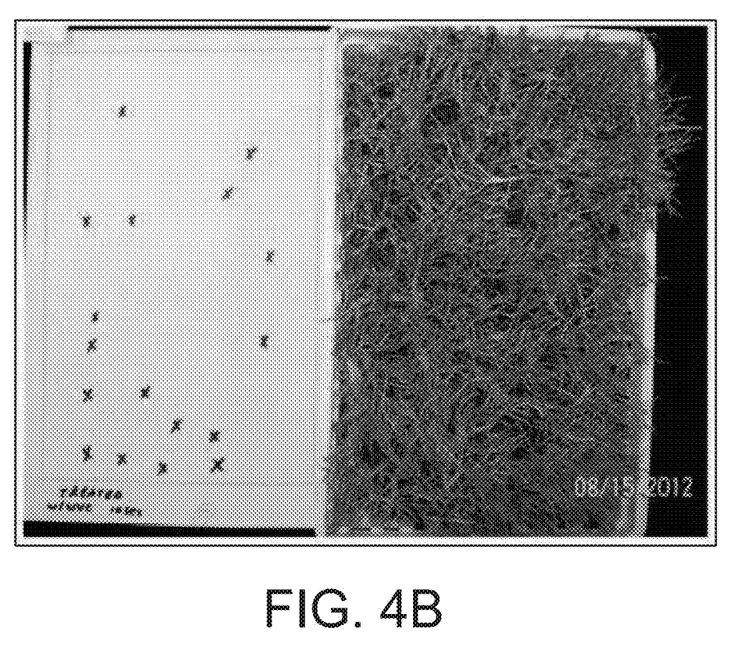
FIG. 4B shows photographs of plants treated with a device to provide UV light to plants.

FIGS. 4A and 4B, shows a second test run to confirm reduction in grass related micro-organisms. The treated sample had only nine instances of very small Mycelium, while the untreated sample had 47 large colonies, which are easily seen with the unaided eye. This treatment resulted in an 80% reduction of dollar spot inoculation using the UV-C treatment. The images of the treated and untreated along with a map of the colony locations are shown. This is followed by an image of the large colonies on the untreated sample. A substantial reduction is a reduction of a least 80 percent of plant pathogens. FIG. 4A shows the mycelium counts of the dollar spot infection post inoculation of the untreated turf grass. FIG. 4B shows the significantly reduced mycelium counts of the dollar spot mycelium post inoculation and after treatment with UV light.

Figure 5:
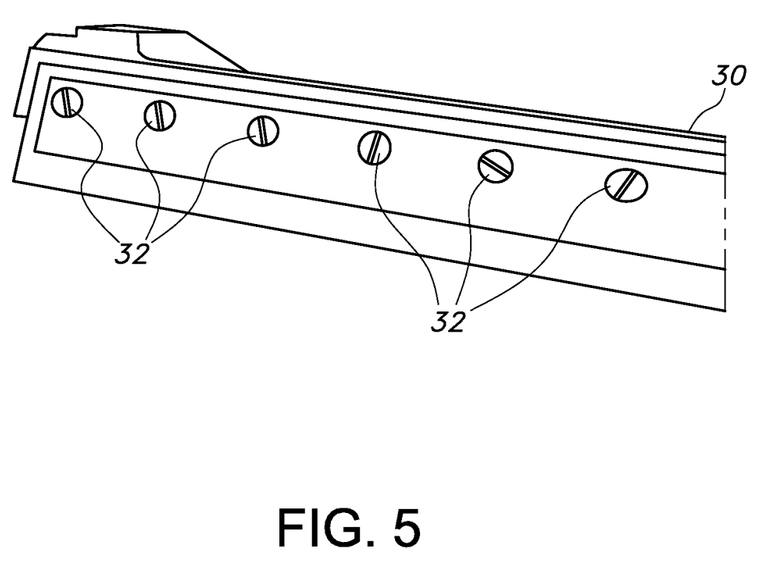
FIG. 5 shows a view of a bed knife with mounting screws.

Table 1 below shows microwatts seconds per $cm_2$ required to kill the pathogen Dollar Spot (*Sclerotinia homoeocarpa*) to a 99% kill rate. It has been determined the use of 30,000 micowatts delivered from a 13 watt output with an intensity factor of three inches above ground level requires 0.562 seconds of time per square centimeter. However, if the UV emitting device was at 1 inch above the surface the radiation is 1.65 Joules/$cm_2$, while at 5 inches the radiation is 8.62 Joules/$cm_2$. The dosage of UV-C radiation in this embodiment ranges from 1.65 Joules/$cm_2$ to 8.62 Joules/$cm_2$.

screws 32 to fix the bed knife blade 30 to the bed knife support 72 and a machined groove 62 to house UV light string 40 and its electrical wiring 60.

Figure 6:
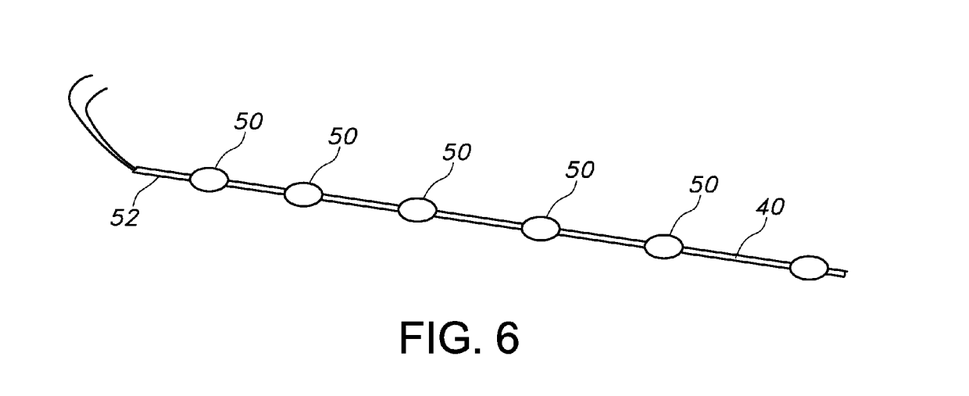
FIG. 6 shows a representation of a light string of this invention.

Now referring to FIG. 6, a UV light string 40 is provided. The UV light string 40 is made up of a plurality of UV emitting devices 50. The UV light is preferably 400-100 nm. In another embodiment the plurality of devices are made of a plurality of semi-conductor illuminating devices, such as an LED. LED lights within UVA wavelength range 400-315 nm and UV (LED and non-LED) lights within UV wavelength range 400-100 nm are contemplated by this invention. It is possible to use a mixture of lights depending on the desired result.

Figure 7:
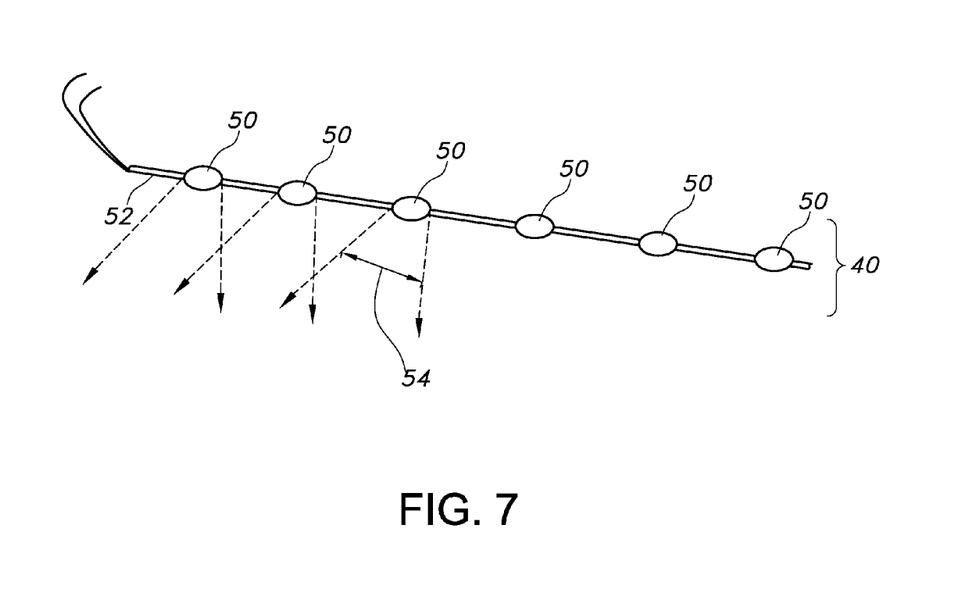
FIG. 7 shows a representation of light arc of the invention.

Now referring to FIG. 7, the plurality of UV emitting devices 50 are positioned to provide a continuous light arc that covers substantially all of the surface to be cut by the

TABLE 1

Microwatts per second to kill dollar spot

| 13 watt output (6 inches) | | | | | 13 watt output (3 inches) | | | | |
| --- | --- | --- | --- | --- | --- | --- | --- | --- | --- |
| seconds per | Factory | *watts | Min. to Kill | 99% | seconds per | Factory | *watts | Kill | 99% |
| 1000 | 12.9 | 503.1 | 1.98767641 | 0.03312794 | 1000 | 22.8 | 889.2 | 1.124606 | 0.0187434 |
| 3000 | 12.9 | 503.1 | 5.96302922 | 0.09938382 | 3000 | 22.8 | 889.2 | 3.373819 | 0.0562303 |
| 6000 | 12.9 | 503.1 | 11.9260584 | 0.19876764 | 6000 | 22.8 | 889.2 | 6.747638 | 0.1124606 |
| 9000 | 12.9 | 503.1 | 17.8890877 | 0.29815146 | 9000 | 22.8 | 889.2 | 10.12146 | 0.168691 |
| 12000 | 12.9 | 503.1 | 23.8521169 | 0.39753528 | 12000 | 22.8 | 889.2 | 13.49528 | 0.2249213 |
| 15000 | 12.9 | 503.1 | 29.8151461 | 0.4969191 | 15000 | 22.8 | 889.2 | 16.8691 | 0.2811516 |
| 18000 | 12.9 | 503.1 | 35.7781753 | 0.59630292 | 18000 | 22.8 | 889.2 | 20.24291 | 0.3373819 |
| 21000 | 12.9 | 503.1 | 41.7412045 | 0.69568674 | 21000 | 22.8 | 889.2 | 23.61673 | 0.3936122 |
| 24000 | 12.9 | 503.1 | 47.7042338 | 0.79507056 | 24000 | 22.8 | 889.2 | 26.99055 | 0.4498426 |
| 27000 | 12.9 | 503.1 | 53.667263 | 0.89445438 | 27000 | 22.8 | 889.2 | 30.36437 | 0.5060729 |
| 30000 | 12.9 | 503.1 | 59.6302922 | 0.9938382 | 30000 | 22.8 | 889.2 | 33.73819 | 0.5623032 |
| | Travel | 3.67720135 | | | | Travel | 2.080522 | | |
| 9 watt output (3 inches) | | | | | 9 watt output (10 inches) | | | | |
| seconds per | Factory | *watts | Min. to Kill | 99% | seconds per | Factory | *watts | Kill | 99% |
| 1000 | 22.8 | 615.6 | 1.62443145 | 0.02707386 | 1000 | 7.94 | 214.38 | 4.664614 | 0.0777436 |
| 3000 | 22.8 | 615.6 | 4.87329435 | 0.08122157 | 3000 | 7.94 | 214.38 | 13.99384 | 0.2332307 |
| 6000 | 22.8 | 615.6 | 9.74658869 | 0.16244314 | 6000 | 7.94 | 214.38 | 27.98769 | 0.4664614 |
| 9000 | 22.8 | 615.6 | 14.619883 | 0.24366472 | 9000 | 7.94 | 214.38 | 41.98153 | 0.6996921 |
| 12000 | 22.8 | 615.6 | 19.4931774 | 0.32488629 | 12000 | 7.94 | 214.38 | 55.97537 | 0.9329228 |
| 15000 | 22.8 | 615.6 | 24.3664717 | 0.40610786 | 15000 | 7.94 | 214.38 | 69.96921 | 1.1661536 |
| 18000 | 22.8 | 615.6 | 29.2397661 | 0.48732943 | 18000 | 7.94 | 214.38 | 83.96306 | 1.3993843 |
| 21000 | 22.8 | 615.6 | 34.1130604 | 0.56855101 | 21000 | 7.94 | 214.38 | 97.9569 | 1.632615 |
| 24000 | 22.8 | 615.6 | 38.9863548 | 0.64977258 | 24000 | 7.94 | 214.38 | 111.9507 | 1.8658457 |
| 27000 | 22.8 | 615.6 | 43.8596491 | 0.73099415 | 27000 | 7.94 | 214.38 | 125.9446 | 2.0990764 |
| 30000 | 22.8 | 615.6 | 48.7329435 | 0.81221572 | 30000 | 7.94 | 214.38 | 139.9384 | 2.3323071 |
| Theory: | Travel | 3.00519818 | | | | Travel | 8.629536 | | |

*So far it has taken 60 sec to kill 80% at 9 watt output. Therefore, the dollar spot requires ~30,000 microwatt seconds per $cm^2$ to destroy.

In another embodiment, a lawn mower cuts by the action of blades passing over a stationary 'bed knife' blade. The grass trapped between the action of the reel blades (which are constantly spinning) and the stationary bed knife blade (which remains stationary) is neatly cut.

Now referring to FIGS. 5-8, in this embodiment, a source of UV radiation is mounted to the 'bed knife' blade. A bed knife blade 30 is provided with a plurality of mounting screws 32 or in one embodiment the mounting screws 32 can be added with a wrench and a bed knife screw tool. The mounting screws 32 serve to fix the bed knife blade 30 to the bed knife support 72. Bed knives are currently manufactured with openings for the mounting screws only which allow for attachment to the bed knife support 72. The rest of the bed knife is a flat piece of metal without any other holes, grooves or other machined facets to its underside in its composition.

Bed knives 30, in one embodiment, can be manufactured for the UV bed knife which will incorporate the mounting blade. In the preferred embodiment the angle of coverage is between 0-45°. In operation, this distance is between 0.100 and 2.00 inches.

Figure 8:
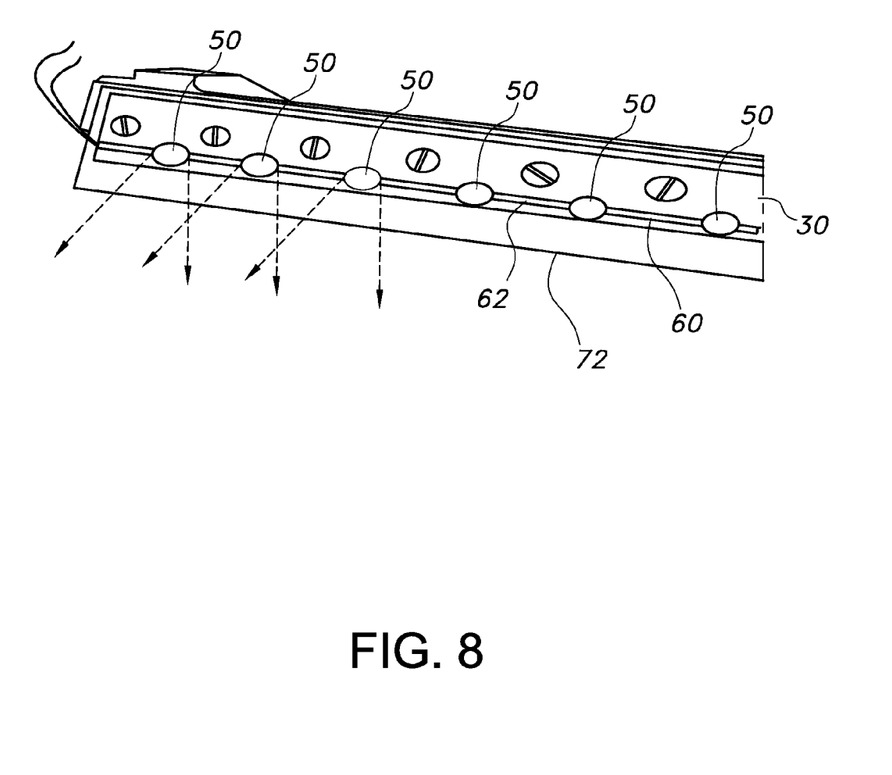
FIG. 8 shows the underside of a bed knife with the present invention

Now referring to FIG. 8, the underside of a bed knife 70 is shown. The UV light string 40 is imbedded in the bed knife blade 30. Each of the devices is connected by an electrical wire 60. The electrical wire 60 is embedded in groove 62.

Figure 9A:
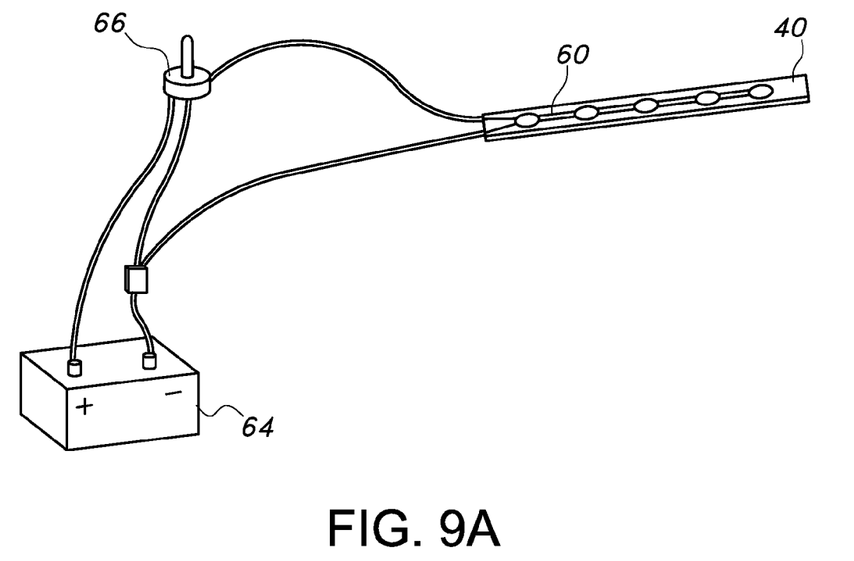
FIG. 9A is a schematic of the electrical diagram of the present invention.
Figure 9B:
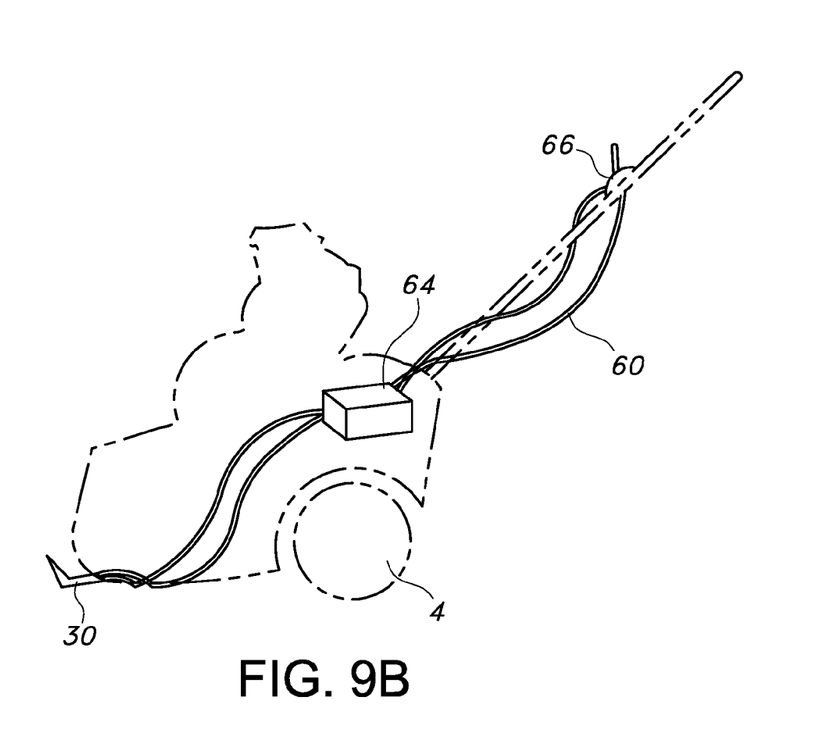
FIG. 9B is a schematic of the electrical diagram of the present invention.

Now referring to FIGS. 9A and 9B, the UV light string 40 is shown removed from the bed knife 70. The UV light string 40 is seen to be connected via wire 60 to a power source 64, such as a battery, generator or alternator, and control unit 66, such as a switch. The control unit 66 may be mounted at a point convenient to the operator 100 so that the UV light string 40 can be turned on or off, as required, for the related portion of the grass cutting task. Control unit 66 may be part of a power management system.

Figure 10:
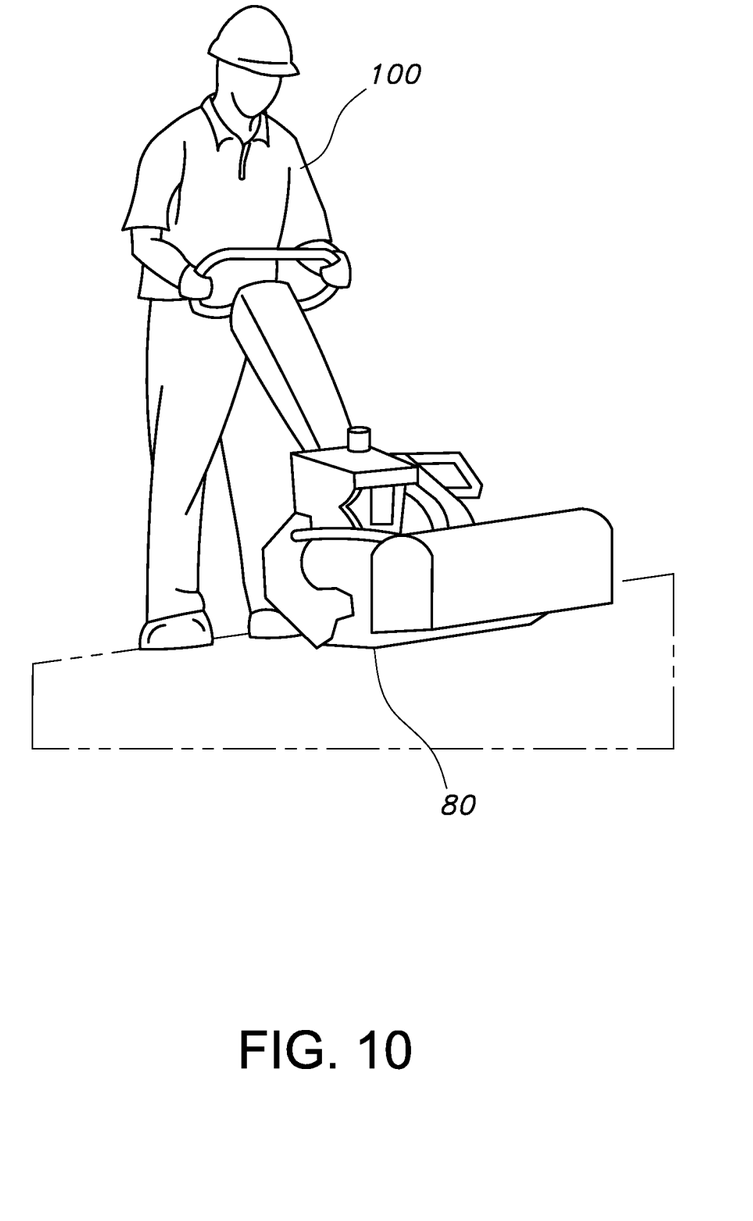
FIG. 10 shows a walk mower that can be used to deliver UV light according to this invention.

Now referring to FIG. 10, a walk mower unit 80 is shown to apply UV light to turf via power supplied by an operator 100. This system is designed for an individual walking behind units consisting of one bed knife and on riding mowing units; however, in another embodiment, riding mowing units contain one or more cutting units and bed knives are contemplated. Each bed knife blade 30 on a multiple reel cutting unit is to be outfitted in a similar manner with: a) an individual power supply 64, light strip 40 and LED switch 66 for each bed knife blade 30; or b) multiple bed knife blades 30 pigtailed together with an electrical wiring plan so as to utilize one or more power supply 64 and LED switch(es) 66.

Dollar Spot Pathogen

Figure 11:
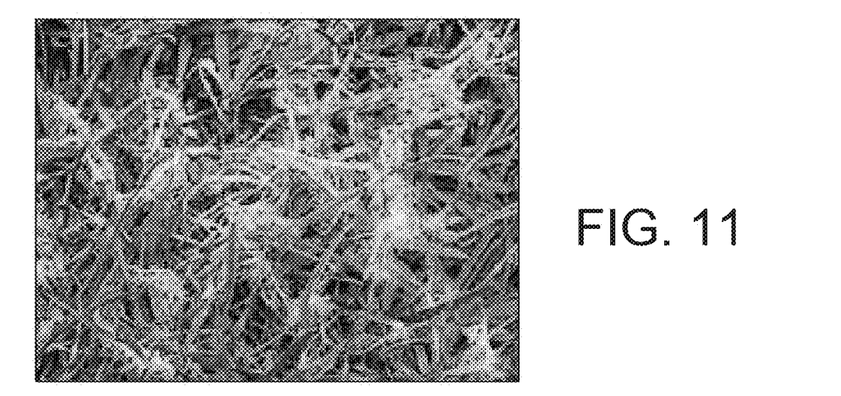
FIG. 11 shows Dollar Spot foliar disease on turf grass.
Figure 12A:
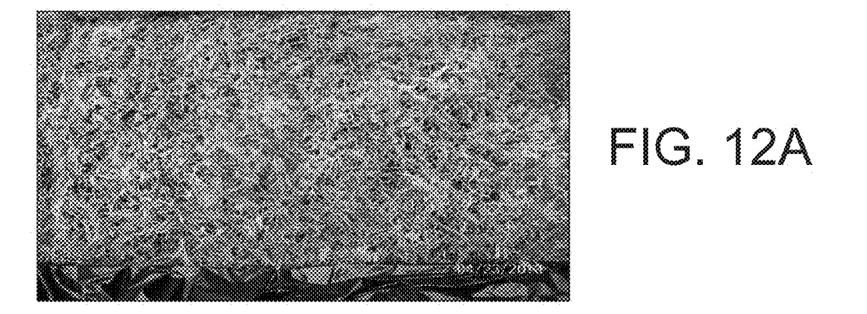
FIG. 12A shows photograph of control plants.
Figure 12B:
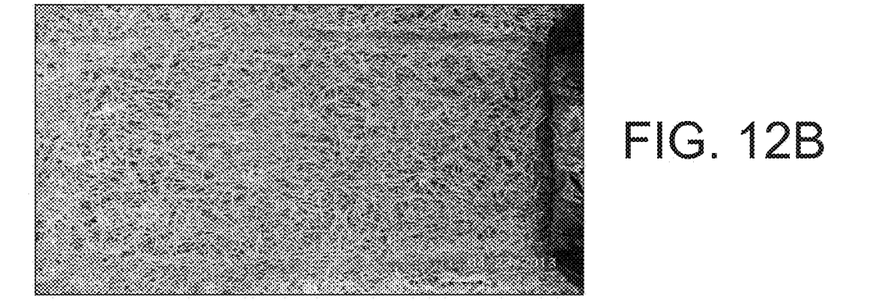
FIG. 12B shows photograph of treated plants.
Figure 12C:
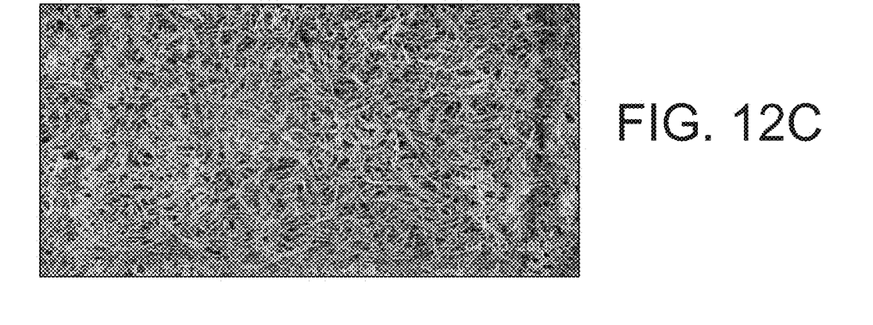
FIG. 12C shows photograph of untreated plants.
Figure 13A:
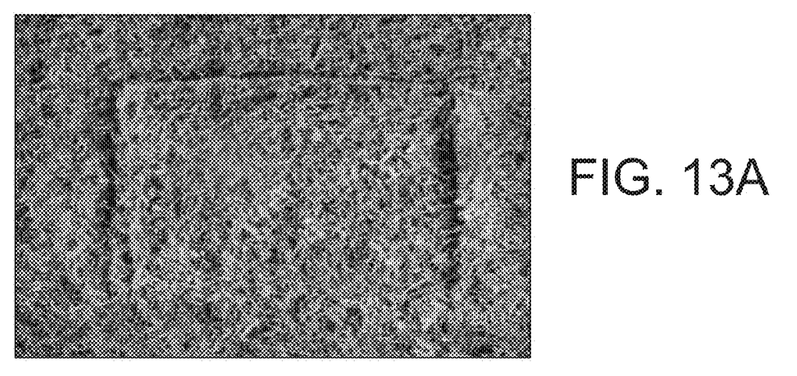
FIG. 13A shows photograph of control plants.
Figure 13B:
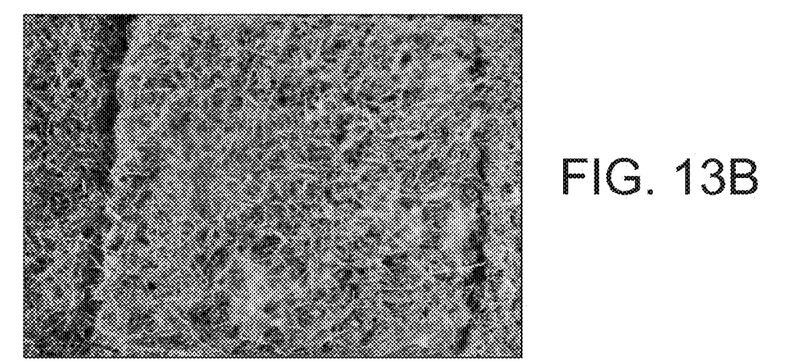
FIG. 13B shows photograph of treated plants.
Figure 13C:
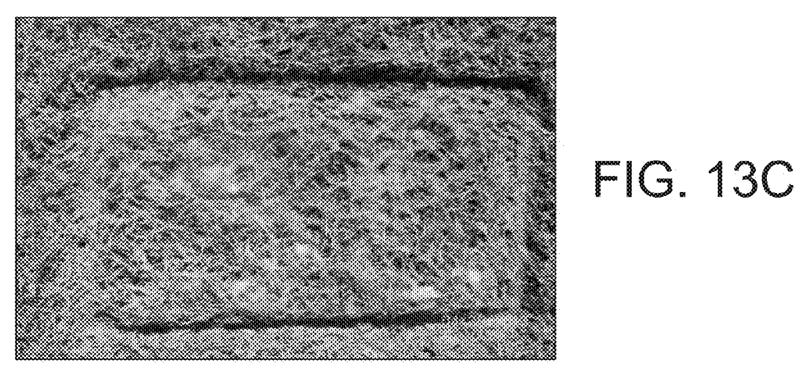
FIG. 13C shows photograph of untreated plants.

Three plots were used to evaluate the effectiveness of LED UV light treatment for Dollar Spots (*Sclerotinia homoeocarpa*) on warm season turf grass. (Apr. 22, 2013). The plots were label: Control: Not treated with *Sclerotinia homoeocarpa* nor LED UV Light (FIG. 12A). Treated: Treated with *Sclerotinia homoeocarpa* and LED UV Light for 10 seconds (FIG. 12B). Untreated: Treated with *Sclerotinia homoeocarpa*, but not LED UV Light (FIG. 11C). The plots were covered with black box to rapidly promote the growth of mycelium dollar spots by increasing moisture, heat and humidity favorable to the growth of the pathogen. Dollar spot is a foliar disease of turf grass. Affected grasses exhibit white to straw-colored lesions that progress downward from the leaf tip or laterally across leaf blades. Grayish-white, cottony mycelium often forms on infected grass blades in the early morning hours when dew is present. (FIG. 11). Plots were evaluated again on Apr. 29, 2013 and several mycelium colonies were visible on both the treated and untreated plots. No mycelium was ever observed on the control plot. The treated and untreated plots were treated again with LED UV lamp for 20 seconds. (FIGS. 13A, 13B and 13C). Mycelium was counted for several days. The mycelium started to grow together after several days and difficult to count in colonies or patches.

TABLE 2

|  | Control | Treated | Untreated |
| --- | --- | --- | --- |
| Apr. 22, 2013 | 0 | 0 | 0 |
| Apr. 23, 2013 | 0 | 0 | 0 |
| Apr. 24, 2013 | 0 | 0 | 0 |
| Apr. 25, 2013 | 0 | 0 | 0 |
| Apr. 26, 2013 | 0 | 2 | 6 |
| Apr. 29, 2013 | 0 | 21 | 35 |
| Apr. 30, 2013 | 0 | 12 | 30 |
| May 1, 2013 | 0 | 2 | 30 |
| May 2, 2013 | 0 | 0 | 21 |

Figure 14A:
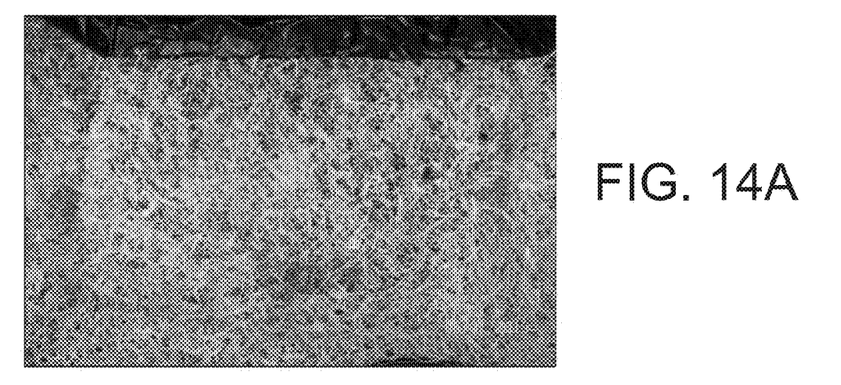
FIG. 14A shows photograph of control plants.
Figure 14B:
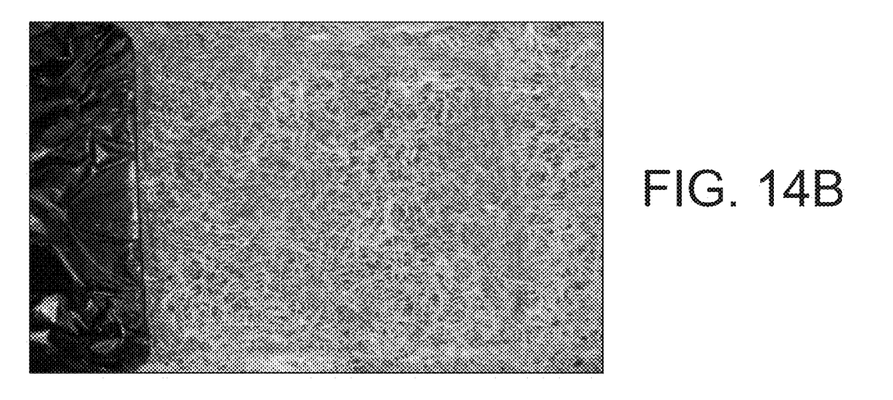
FIG. 14B shows photograph of treated plants.
Figure 14C:
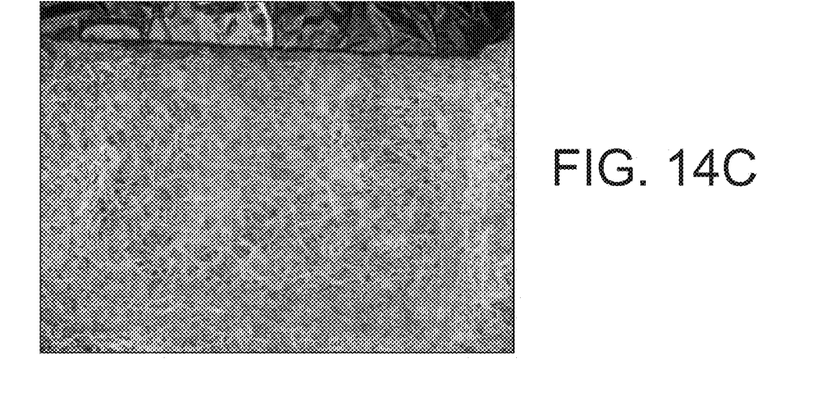
FIG. 14C shows photograph of untreated plants.

Observations of the plot exhibited drastic reduction of mycellium on the treated plot while the untreated plot revealed many visible colonies. (FIGS. 14A, 14B, 14C). The LED lights we used in this experiment were (6) 1 watt bulbs at 380-400 nm for 10 seconds. Based on this, 60 joules/cm$_2$ on a 10 second duration was supplied.

Figure 15A:
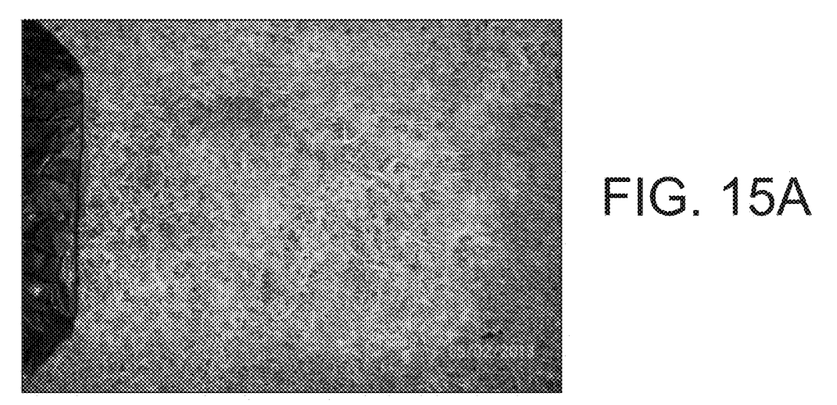
FIG. 15A shows photograph of control plants.
Figure 15B:
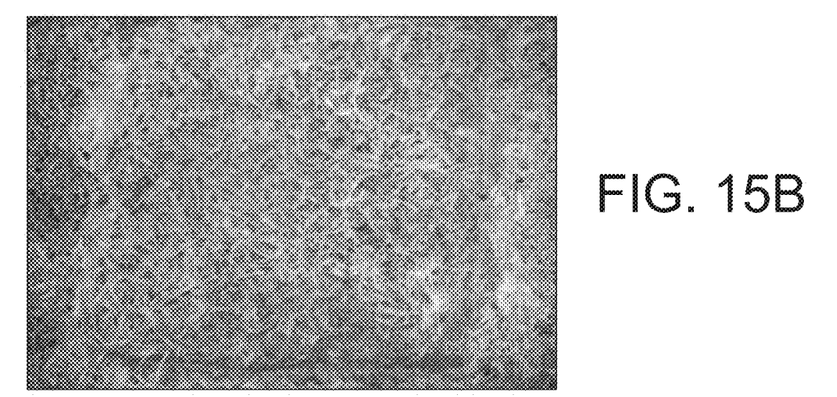
FIG. 15B shows photograph of treated plants.
Figure 15C:
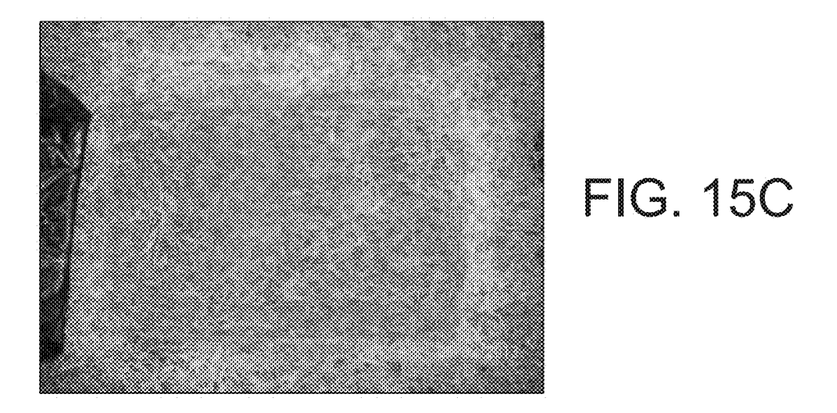
FIG. 15C shows photograph of untreated plants.

Most of the inoculated turf was severely damaged by May 2, 2013. However, the untreated plot still had many colonies of mycelium, while the treated plot had green grass and viable tissue remaining (FIGS. 15A, 15B and 15C).

The temperature during treatment and observation was 70-85° F. There was moisture or dew on the grass in the morning.

By embedding UV lights in a bed knife, 99% kill of Dollar Spot, at a height of ⅛" above ground level with a 50.1 intensity factor at 0.255898 seconds on 30,000 microwatts, can be achieved. Intensity level is calculated as follows: there is 9.5 intensity per inch. Therefore, at 1 inches the intensity is 32.3 (@2 in)+9.5=41.8 and 51.3 at zero inches (divide 9.5/0.125 inch is 1.19 intensity for each 118$^{th}$ of an inch or 50.1 intensity factor).

These and other aspects, features and advantages of the invention will be understood with reference to the detailed description herein, and will be realized by means of the various elements and combinations particularly pointed out in the appended claims. It is to be understood that both the foregoing general description and the following detailed description of the invention are exemplary and explanatory of preferred embodiments of the invention, and are not restrictive of the invention, as claimed.

The invention claimed is:

1. A hand propelled device for reducing the total number of pathogens of one or more pathogen living in plants selected from the group consisting: of turf, foliage, flowers or shrubs comprising: a frame connector connected to a handle at one end and a UV emitting device at a second end, wherein said UV emitting device provides a sufficient level of radiation necessary to reduce the total number of pathogens of one or more pathogen living in the plants without killing said plants and a light shroud of sufficient size to protect an operator from UV radiation and a power source to operate said device wherein the frame connector is fixedly positioned above the UV emitting device and the frame connector is positioned to allow the handle to be grasped by a user's hand, wherein said handle includes a control mechanism.

2. The device of claim 1 wherein the wave light of the light is about 400-100 nm.

3. The device of claim 1 wherein the dosage of radiation emitted from the device ranges from about 1.65 to 8.62 Joules/cm$_2$.

4. The device of claim 1 wherein said frame connector is a tube.

5. A process to for reducing the total number of pathogens of one or more pathogen living in plants selected from the group consisting: of turf, foliage, flowers or shrubs, comprising the steps of:

providing force from a user's hand to a hand propelled device made of: a frame connector connected to a handle at one end and a UV emitting device at a second end wherein said handle includes a control mechanism, wherein said UV emitting device provides a sufficient level of radiation necessary to reduce the total number of pathogens of one or more pathogen living in the plants without killing said plants and a light shroud of sufficient size to protect the user from UV radiation and a power source to operate said device wherein the frame connector is fixedly positioned above the UV emitting device and the frame connector is positioned to allow the handle to be grasped by a user's hand, to move the hand propelled device away from an origin of a force applied by the user hand to provide UV radiation to said plants.

* * * * *